(12) United States Patent
Srivastava et al.

(10) Patent No.: US 8,742,028 B2
(45) Date of Patent: Jun. 3, 2014

(54) SOLID SUPPORT FOR FMOC-SOLID PHASE SYNTHESIS OF PEPTIDE ACIDS

(75) Inventors: Kripa S. Srivastava, Chesterfield, MO (US); Matthew R. Davis, St. Louis, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 793 days.

(21) Appl. No.: 12/773,324

(22) Filed: May 4, 2010

(65) Prior Publication Data

US 2010/0286359 A1    Nov. 11, 2010

Related U.S. Application Data

(60) Provisional application No. 61/175,808, filed on May 6, 2009.

(51) Int. Cl.
| | |
|---|---|
| C08F 8/00 | (2006.01) |
| C08F 8/10 | (2006.01) |
| C08F 8/04 | (2006.01) |
| C07K 1/04 | (2006.01) |

(52) U.S. Cl.
USPC ........... 525/384; 525/383; 525/385; 525/386; 525/54.1; 525/54.11; 525/332.9; 525/333.3; 530/334

(58) Field of Classification Search
USPC ............... 525/54.1, 54.11, 332.9, 333.3, 383, 525/384, 385, 386; 530/334
See application file for complete search history.

(56) References Cited

U.S. PATENT DOCUMENTS

| 4,859,736 A | * | 8/1989 | Rink | ............... 525/54.1 |
| 5,004,781 A | | 4/1991 | Rink | |
| 5,268,423 A | * | 12/1993 | Joran | ............. 525/54.11 |

FOREIGN PATENT DOCUMENTS

| EP | 0285562 A2 | 10/1988 |
| WO | 9317056 A1 | 9/1993 |

OTHER PUBLICATIONS

Chang et al., "Solid-Phase Peptide Synthesis Using Mild Base Cleavage of Nα- Fluorenylmethyloxycarbonylamino Acids, Exemplified by a Synthesis of Dihydrosomatostatin", IJPPR, 11, 1978, pp. 246-249.
Wang, "p-Alkoxybenzyl Alcohol Resin and p-Alkoxybenzyloxycarbonylhydrazide Resin for Solid Phase Synthesis of Protected peptide Fragments" JACS, 95(4), 1973, pp. 1328-1333.
Wang,"Solid-Phase Synthesis of Protected peptide Hydrazides. Preparation and Application of Hydroxymethyl Resin and 3-(p-Benzyloxypehnyl)-1,1-dimethylpropyloxycarbonylhydrazide Resin", JOC, 40(9), 1975, pp. 1235-1239.
Atherton et al., "A Mild Procedure for Solid Phase Peptide Synthesis: Use of Fluorenylmethoxycarbonylamino-acids", JCS, Chem. Comm., 1978, pp. 537-539.
Barlos et al., "2-Chlorotrityl chloride resin", IJPPR, 37, 1991, pp. 513-520.
Barlos et al., "Application of 2-chlorotrityl residn in solid phase synthesis of (Leu14)-gastrin I and unsulfated cholecystokinin octapeptide", IJPPR, 38, 1991, p. 555-561.
Sieber, "An Improved method for anchoring of 9-Fluorenylmethoxycarbonyl-Amino Acids to 4-Alkoxybenzyl Alcohol Resins", Tetrahedron Letters, 28(49), 1987, pp. 6147-6150.
Wang et al., "Preparation of Protected peptide Intermediates for a synthesis of the Ovine Pituitary Growth Hormone Sequence 96-135", JOC, 40(9), 1975, pp. 1227-1234.
Atherton et al., "Racemisation of Activated, Urethane-protected Amino-acids by p-Dimethyl-aminopyridine. Significance in Solid-phase Peptide Synthesis", JCS, Chem. Comm., 1981, p. 336-337.
Fuller et al., "Esterification of 4-Alkoxybenzyl Alcohol Resin With FMOC-Histidine(N™-Trityl)-N-Carbocxyanhydride", Tetrahedron Letters, 35(27), 1994, pp. 4673-4676.
Rink, "Solid-Phase Synthesis of Protected Peptide Fragments Using a Trialkoxy-Diphenyl-Methylester Resin," Tetrahedron Letters, 1987, vol. 28, No. 33, p. 3787-3790.
Aldrich Advanced Science, Jan. 1, 2006, p. 271 and 1599.

* cited by examiner

Primary Examiner — Roberto Rabago

(57) ABSTRACT

The present invention provides a solid support for Fmoc-solid phase synthesis of peptides. In particular, the solid supports of the invention may be utilized to produce peptide acids.

6 Claims, No Drawings

SOLID SUPPORT FOR FMOC-SOLID PHASE SYNTHESIS OF PEPTIDE ACIDS

CROSS REFERENCE TO RELATED APPLICATIONS

This application claims the benefit of U.S. Provisional Application No. 61/175,808 filed May 6, 2009, which is incorporated herein in its entirety.

FIELD OF THE INVENTION

The invention provides a solid support for Fmoc-solid phase synthesis of peptides. In particular, the solid supports may be utilized to produce peptide acids.

BACKGROUND OF THE INVENTION

Polypeptide synthesis may be either solid-phase synthesis (SPPS) or solution-phase synthesis (SP). Progress in solid phase peptide synthesis (SPPS) has always been stimulated by the introduction of new chemistries and new solid supports. Unlike ribosome protein synthesis, protein synthesis by SPPS generally proceeds from the C-terminus to N-terminus. There are several groups of peptides and peptidomimetic compounds characterized by derivatization at the C-terminus of the peptide chain. These groups include several commercially and therapeutically important peptide-acids.

There are several solid supports commercially available for the synthesis of peptide-acids. Presently, two main chemistries used for their synthesis are Boc/Benzyl and Fmoc/t.Butyl chemistry. Recently, Fmoc-chemistry has become preferred over Boc-chemistry because of its greater environmental safety due to avoidance of hazardous and highly toxic hydrofluoric acid, and the use of mild conditions. The most common solid supports for the synthesis of peptide-acids employing Fmoc/t.Butyl chemistry are 4-hydroxymethylphenyloxymethyl polystyrene resin developed by Wang (S. S. Wang, JACS, 95, 1328-1333, 1973; JOC, 40, 1235-1239, 1975), 4-hydroxymethylphenoxyacetyl-poly(dimethylactylamide) resin developed by Atherton (E. Atherton, et al, JCS, Chem. Comm., 1978, 537-539), and 2-chlorotritylchloride (CTC) resin developed by K. Barlos (K. Barlos, et al, IJPPR, 37, 513-520, 1991; 38, 555, 1991).

Each of the commonly utilized resins for the production of peptide acids, however, suffers from drawbacks. First, the preparation of these resins is cumbersome and expensive. Next, the resins often fail to produce the desired peptide in sufficient yield and purity. Finally, acid peptides synthesized using these resins are prone to racemization. A need therefore exists for a solid support that is economical to produce, and that can be used for Fmoc-SPPS synthesis of peptide acids in both high purity and yield with only negligible racemization.

SUMMARY OF THE INVENTION

Briefly, therefore, the present invention provides solid supports that may be utilized for Fmoc-SPPS synthesis of peptide acids. In one aspect, the solid support encompasses a compound comprising Formula (I):

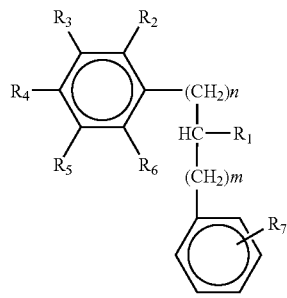

wherein:
$R^1$ is $OR^8$;
$R^2$, $R^3$, $R^4$, $R^5$, and $R^6$ are independently selected from the group consisting of hydrogen, hydrocarbyl, and substituted hydrocarbyl, provided, however, that at least two of $R^2$, $R^3$, $R^4$, $R^5$, and $R^6$ are other than hydrogen;
$R^7$ and the phenyl ring to which it is attached together comprise a solid support comprising at least one polymer;
$R^8$ is selected from the group consisting of hydrogen, a protecting group, an amino acid residue, a hydrocarbyl, a substituted hydrocarbyl, and a peptide; and
n and m are independently integers from 0 to 5.

In another iteration the invention encompasses a synthetic route for the production of a solid support comprising Formula (I). The process comprises the formation of a compound comprising Formula (I) according to Reaction Scheme 1:

Reaction Scheme 1:

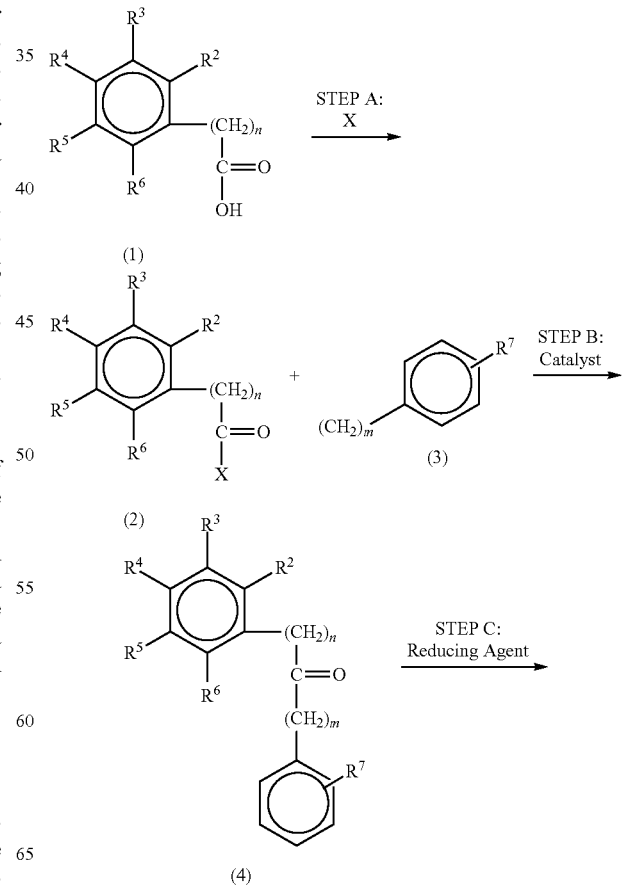

-continued

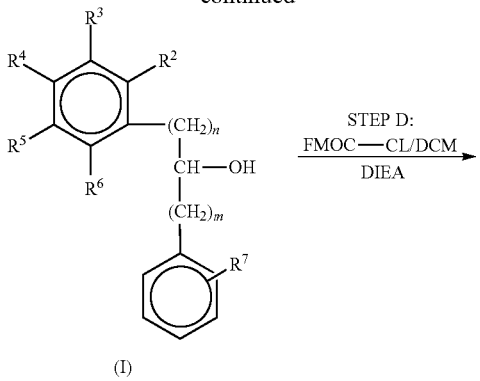

(I)

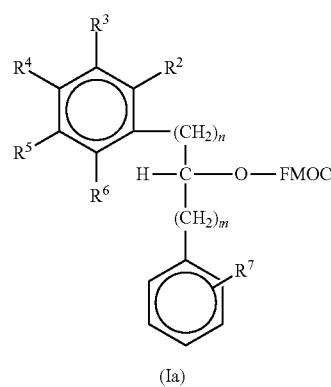

(Ia)

wherein:

$R^2$, $R^3$, $R^4$, $R^5$, and $R^6$ are independently selected from the group consisting of hydrogen, hydrocarbyl, and substituted hydrocarbyl, provided, however, that at least two of $R^2$, $R^3$, $R^4$, $R^5$, and $R^6$ are other than hydrogen;

$R^7$ and the phenyl ring to which it is attached together comprise a solid support comprising at least one polymer;

n and m are independently integers from 0 to 5; and

X comprises a halogen.

In an additional iteration, the invention encompasses a method for the production of a peptide. The method comprises:

(a) activating the carboxy group of an amino acid that has its amine protected by a Fmoc group, and its side chain protected by an acid labile group;

(b) coupling the activated amino acid to a solid support comprising Formula (I):

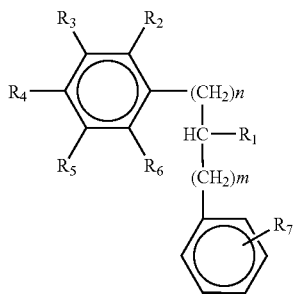

(I)

wherein:

$R^1$ is $OR^8$;

$R^2$, $R^3$, $R^4$, $R^5$, and $R^6$ are independently selected from the group consisting of hydrogen, hydrocarbyl, and substituted hydrocarbyl, provided, however, that at least two of $R^2$, $R^3$, $R^4$, $R^5$, and $R^6$ are other than hydrogen;

$R^7$ and the phenyl ring to which it is attached together comprise a solid support comprising at least one polymer;

$R^8$ is selected from the group consisting of hydrogen, a protecting group, a hydrocarbyl, and a substituted hydrocarbyl; and n and m are independently integers from 0 to 5;

(c) treatment of the solid support with a base to deprotect the amine group of the amino acid protected with Fmoc; and (d) repeating steps (a) to (c) until the target polypeptide is synthesized.

Other aspects and iterations of the invention are described in more detail below.

DETAILED DESCRIPTION OF THE INVENTION

A solid support has been developed that can be utilized to produce peptides using Fmoc-SPPS. While the solid support may be utilized to produce a variety of peptides, it is particularly useful for the synthesis of peptide acids (e.g., Linaclotide and PT-141 (Bremelanotide)). As illustrated in Table 7 of the examples, the solid support of the invention generally produces peptides in higher yield and purity compared to other commercially available solid supports commonly used to synthesize peptide acids, such as the Wang resin. The invention also encompasses a process to make the solid support in an economical manner using a three-step reaction scheme.

(I) Solid Support

The solid support of the invention generally comprises a polymeric resin covalently conjugated to a linker. In one embodiment, the solid support is a compound comprising Formula (I):

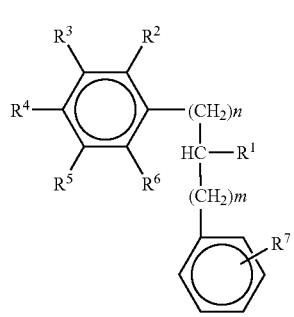

(I)

wherein:

$R^1$ is $OR^8$;

$R^2$, $R^3$, $R^4$, $R^5$, and $R^6$ are independently selected from the group consisting of hydrogen, hydrocarbyl, and substituted hydrocarbyl, provided, however, that at least two of $R^2$, $R^3$, $R^4$, $R^5$, and $R^6$ are other than hydrogen;

$R^7$ and the phenyl ring to which it is attached together comprise a solid support comprising at least one polymer;

$R^8$ is selected from the group consisting of hydrogen, a protecting group, an amino acid residue, a hydrocarbyl, a substituted hydrocarbyl, and a peptide; and n and m are independently integers from 0 to 5.

In one embodiment for compounds comprising Formula (I), at least two of $R^2$, $R^3$, $R^4$, $R^5$, and $R^6$ are the same moiety selected from the group consisting of {—}$(CH_2)_5CH_3$ and {—}O(CH$_2$)$_s$CH$_3$, wherein s is an integer from 0 to 5. Stated another way, at least two of R$^2$, R$^3$, R$^4$, R$^5$, and R$^6$ comprise {—}(CH$_2$)$_s$CH$_3$. Alternatively, at least two of R$^2$, R$^3$, R$^4$, R$^5$, and R$^6$ comprise {—}O(CH$_2$)$_s$CH$_3$. In certain alternatives of this embodiment, three of R$^2$, R$^3$, R$^4$, R$^5$, and R$^6$ are hydrogen. In other alternatives of this embodiment, two of R$^2$, R$^3$, R$^4$, R$^5$, and R$^6$ are hydrogen. In one preferred embodiment, s is an integer from 0 to 2. In another preferred alternative of this embodiment, s is 0.

In one exemplary embodiment for compounds comprising Formula (I), R$^2$ and R$^4$ are each {—}(CH$_2$)$_s$CH$_3$. Alternatively, R$^2$ and R$^4$ are each {—}(CH$_2$)$_s$CH$_3$. In each aspect of this embodiment, s is an integer from 0 to 5, more preferably, from 0 to 2, and still more preferably 0. In one alternative, R$^3$, R$^5$, and R$^6$ are each hydrogen.

In yet another exemplary embodiment for compounds comprising Formula (I), R$^4$ and R$^6$ are each {—}(CH$_2$)$_s$CH$_3$. Alternatively, R$^4$ and R$^6$ are each {—}O(CH$_2$)$_s$CH$_3$. In each aspect of this embodiment, s is an integer from 0 to 5, more preferably, from 0 to 2, and still more preferably 0. In one alternative, R$^2$, R$^3$, and R$^5$ are each hydrogen.

In still another exemplary embodiment for compounds comprising Formula (I), R$^2$, R$^3$, and R$^4$ are each {—}(CH$_2$)$_s$CH$_3$ Alternatively, R$^2$, R$^3$, and R$^4$ are each {—}O(CH$_2$)$_s$CH$_3$. In each aspect of this embodiment, s is an integer from 0 to 5, more preferably, from 0 to 2, and still more preferably 0. In one alternative, R$^5$ and R$^6$ are each hydrogen.

In another exemplary embodiment for compounds comprising Formula (I), R$^4$, R$^5$, and R$^6$ are each H(CH$_2$)$_s$CH$_3$. Alternatively, R$^4$, R$^5$, and R$^6$ are each {—}O(CH$_2$)$_s$CH$_3$. In each aspect of this embodiment, s is an integer from 0 to 5, more preferably, from 0 to 2, and still more preferably 0. In one alternative, R$^2$ and R$^3$ are each hydrogen.

For each of the foregoing embodiments, R$^7$, the solid support, may be comprised of one or more suitable polymeric materials that comprise phenyl groups in its backbone. Suitable solid supports include, but are not limited to, polyacrylamide, polystyrene, polyacrylate, hydroxethylmethacrylate, polyamide, polyethylene, polyethyleneoxy, or copolymers and grafts of such. In an exemplary embodiment, the material is a synthetic polymer of styrene. To increase the stability and insolubility in organic solvents, typically the polystyrene resin will be cross-linked with divinylbenzene, for example, using from about 0.5% to about 2% divinylbenzene. While the size and shape of the resin can and will vary, typically the resin will have a spherical shape and display a broad particle size distribution in the range of about 20 µm to about 150 µm. Stated another way, the size may range from about 100 mesh to about 400 mesh.

In each of the foregoing embodiments, R$^1$ comprises OR$^8$. As detailed above, R$^8$ is selected from the group consisting of hydrogen, a protecting group, an amino acid residue, a hydrocarbyl, a substituted hydrocarbyl, and a peptide. In one alternative embodiment, R$^8$ is selected from the group consisting of hydrogen, Fmoc, an amino acid residue, and a peptide. In one exemplary embodiment, R$^8$ is hydrogen. In another exemplary embodiment, R$^8$ is Fmoc. In still another exemplary embodiment, R$^8$ is an amino acid residue. In an additional exemplary embodiment, R$^8$ is a peptide. The amino acid residue or peptide may be protected or unprotected.

For each of the foregoing embodiment, the integers, n and m may independently be 0 to 5. In one embodiment, n and m are independently 0 to 2. In still another embodiment, n and m are 1. In yet another embodiment, n and m are 0.

In an exemplary embodiment, the compound comprising Formula (I) comprises the following structure:

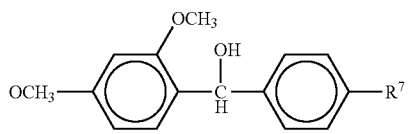

In yet another exemplary embodiment, the compound comprising Formula (I) comprises the following structure:

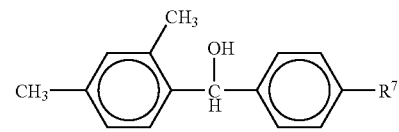

(II) Process for Making the Solid Support

As will be appreciated by a skilled artisan, the synthetic route used to produce the solid support comprising Formula (I) can and will vary without departing from the scope of the invention. The solid support may be made in accordance with Reaction Scheme 1 shown below.

Referring to Reaction Scheme 1, the compound comprising Formula (I) may be made via a three-step reaction scheme. By way of non-limiting example, when R$^1$ is OH, the synthetic route may comprise (1) step A that encompasses halogenation of a carboxylic acid group to convert compound 1 to compound 2; (2) step B that involves covalent conjugation of compound 2 to a polymeric material comprising compound 3 to produce a ketone comprising compound 4; and (3) step C that encompasses reduction of the carbonyl group of compound 4 to produce an iteration of the solid support of the invention comprising Formula (I). The compound comprising Formula (I) may be further reacted with the protecting group Fmoc to produce the compound comprising Formula (Ia).

Reaction Scheme 1:

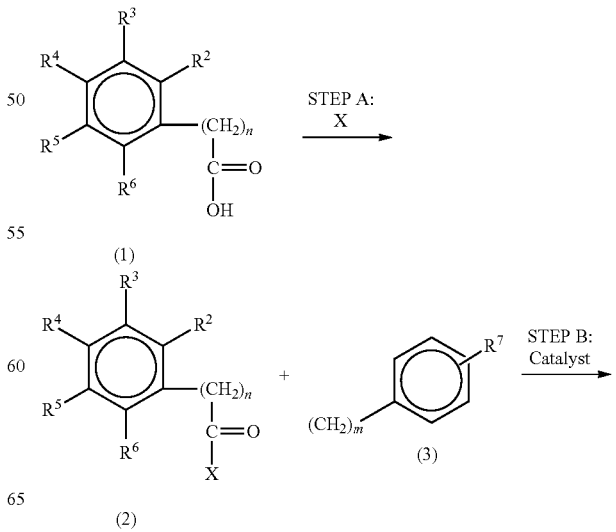

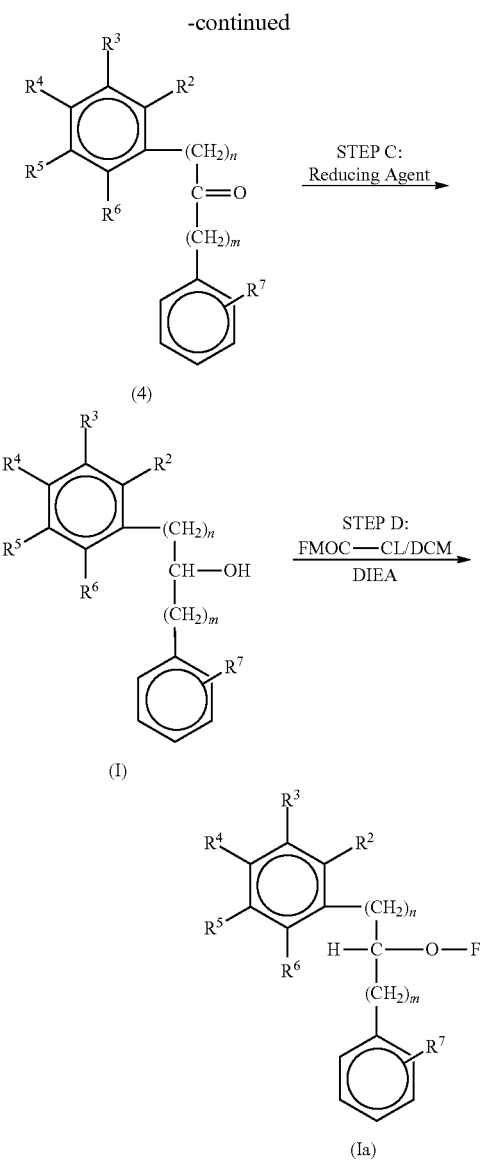

wherein:

R², R³, R⁴, R⁵, R⁶, R⁷, m, and n are as described in section (I) for compounds having Formula (I), and X comprises a halogen.

In step A, compound 1 is contacted with X, which is a compound comprising a halogen. The choice of halogen can and will vary. In one embodiment, the halogen is selected from bromide and chloride. In an exemplary embodiment, the halogen is chloride, such as thionyl chloride (i.e., $SOCl_2$). Generally speaking, the amount of compound 1 to the amount of X may be expressed as a molar ratio of from about 1:2 to about 1:10. In one exemplary embodiment, the amount of compound 1 to the amount of X is a molar ratio of about 1:8.3. In another exemplary embodiment, the amount of compound 1 to the amount of X is a molar ratio of about 1:4. Step A is typically carried out in the presence of an organic solvent. For example, suitable solvents include, but are not limited to, alkane and substituted alkane solvents (including cycloalkanes), aromatic hydrocarbons, esters, ethers, ketones, combinations thereof, and the like. Specific organic solvents that may be employed, include, for example, acetonitrile, benzene, butyl acetate, t-butyl methylketone, chlorobenzene, chloroform, chloromethane, cyclohexane, dichloromethane, dichloroethane, dichloroethene, fluorobenzene, heptane, hexane, isobutylmethylketone, isopropyl acetate, methylethylketone, methyltetrahydrofuran, pentyl acetate, n propyl acetate, tetrahydrofuran, toluene, and combinations thereof. In an exemplary embodiment, step A is carried out in the presence of dichloromethane.

For step B, compound 2 is contacted with compound 3, the polymeric resin, typically in the presence of a catalyst to form compound 4. The catalyst may be a metal catalyst such as aluminum chloride ($AlCl_3$), ferric chloride ($FeCl_3$), and stannic chloride ($SnCl_4$). In a preferred embodiment, the catalyst is $AlCl_3$. The amount of compound 2 to the amount of compound 3 to the amount of catalyst may be expressed as weight ratio of 1:1:1 to about 3:2:1. In one exemplary embodiment, the amount of compound 2 to the amount of compound 3 to the amount of catalyst is a ratio of about 1.4:1.2:1. In another exemplary embodiment, the amount of compound 2 to the amount of compound 3 to the amount of catalyst is a ratio of about 2:1.2:1. Step B is typically carried out in the presence of an organic solvent as described above. In one exemplary embodiment, step A is carried out in the presence of dichloromethane. In another exemplary embodiment, step B is carried out in the presence of dichloroethene.

In step C, the carbonyl of compound 4 is reduced to produce an iteration of the solid support comprising Formula (I). The reducing agent can and will vary. Typically, the reducing agent will be sodium borohydride ($NaBH_4$). Alternatively, the reducing agent may be lithium aluminium hydride ($LiAlH_4$), nascent hydrogen, hydrazine ($N_2H_4$), diisobutylaluminum hydride (DIBAH), oxalic acid ($C_2H_2O_4$), and formic acid (HCOOH). The amount of compound 4 to the amount of reducing agent may be expressed as a weight ratio or 1:1 to 5:1. In an exemplary embodiment, the amount of compound 4 to the amount of reducing agent is a ratio of about 2:1. Step C is typically carried out in the presence of an aprotic solvent, a protic solvent or a combination of aprotic and protic solvents. Suitable examples of aprotic solvents include diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl) ether, N,N-dimethylacetamide (DMAC), 1,4-dioxane, N-methyl-2-pyrrolidinone (NMP), ethyl acetate, ethyl formate, ethyl methyl ketone, formamide, hexachloroacetone, hexamethylphosphoramide, methyl acetate, N-methylacetamide, N-methylformamide, methylene chloride, nitrobenzene, nitromethane, propionitrile, sulfolane, tetramethylurea, tetrahydrofuran (THF), 2-methyl tetrahydrofuran, toluene, trichloromethane, and combinations thereof. Suitable examples of protic solvents include, but are not limited to, methanol, ethanol, isopropanol, n-propanol, isobutanol, n-butanol, s-butanol, t-butanol, formic acid, acetic acid, and combinations thereof. In a preferred embodiment, step C is carried out in a combination of aprotic and protic solvents. In an exemplary embodiment, step C is carried out in a combination of dimethylformamide and methanol. The amount of dimethylformamide to the amount of methanol may be expressed as a volume ratio of 1:1 to 5:1. In an exemplary embodiment, the amount of dimethylformamide to the amount of methanol is a ratio of about 3:1.

The reaction conditions for steps A to C of the process, such as reaction time, temperature, and pH may also vary without departing from the scope of the invention. For step A of the process, by way of non-limiting example, the reaction time may range from several hours to several days, the reaction temperature may range from approximately room temperature to about 0° C., and the reaction is generally conducted at an approximately acid pH. For step B of the process, by way of further non-limiting example, the reaction time may range from about several hours to several days, the reaction temperature is from approximately room temperature to about 0° C., and the reaction is generally conducted at an approximately acid pH. For step C, by way of further non-limiting example, the reaction time may range from about several hours to several days, the reaction temperature is from approximately room temperature to about 80° C. Exemplary reaction parameters for each step of the process are detailed in the examples.

(III) Use of the Solid Support to Synthesize Peptides

As detailed herein, the solid support comprising Formula (I) may be utilized to synthesize a wide range of peptides without departing from the scope of the invention. In general, the solid support may first be loaded with an Fmoc protecting group, or with an Fmoc-protected amino acid group at position $OR^8$ and then the peptide is elongated as illustrated in FIG. 3.

In one embodiment, the solid support may first be loaded with an Fmoc-protected amino acid group at position $OR^8$. Methods of loading the first Fmoc-protected amino acid are known to those skilled in the art and can be found in, for example, Fmoc Solid Phase Peptide Synthesis: A Practical Approach (Practical Approach Series) Oxford University Press, USA; 1 edition (Mar. 2, 2000), which is incorporated herein by reference in its entirety. Non-limiting examples of methods for attaching the first amino acid to the solid support include the symmetrical anhydride method, the dichlorobenzoyl chloride method, DIC-HOBt method, and the MSNT/MeIm method.

In an exemplary embodiment, the first amino acid may be attached to the solid support using the symmetrical anhydride method. As depicted in FIG. 1 below, in this method when $R^1$ is OH, a symmetrical anhydride is first produced. The symmetrical anhydride is then reacted with the solid support to produce a solid support comprising a compound of Formula (I), with an Fmoc-protected amino acid.

FIG. 1

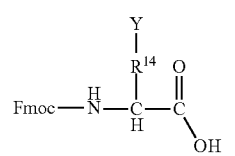

Incoming amino acid with Y side chain protecting group

Activation (DIC)

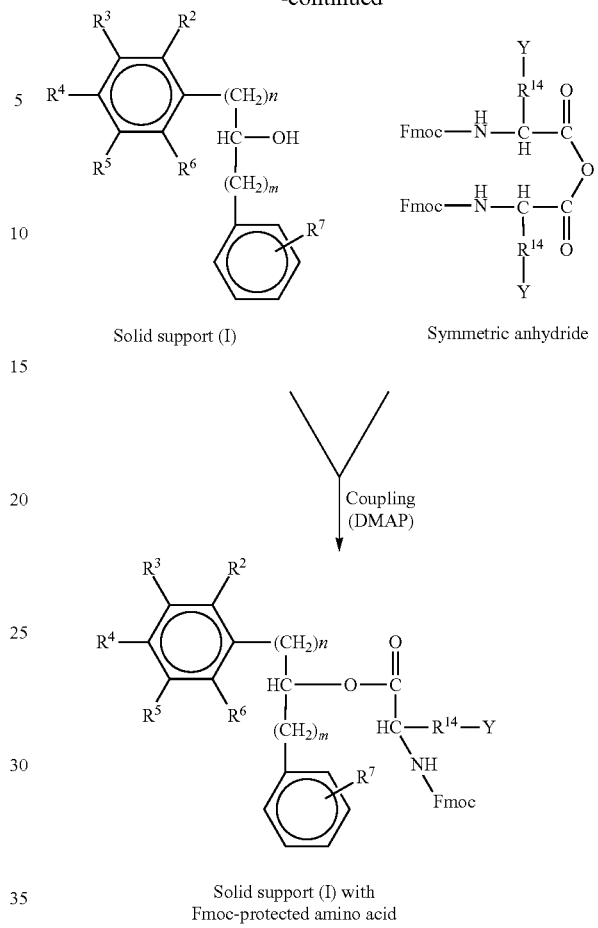

Solid support (I) with Fmoc-protected amino acid wherein:
$R^2$, $R^3$, $R^4$, $R^5$, $R^6$, $R^7$, m, and n are as described in section (I) for compounds having Formula (I).

The symmetrical anhydride may be produced by reacting an Fmoc-protected amino acid with a carbodiimide. Non-limiting examples of carbodiimides suitable for producing symmetrical anhydrides may include dicyclohexylcarboimide (DCC), 1-ethyl-3-(3-dimethylaminopropyl)carbodiimide hydrochloride (EDC) or diisopropylcarboimide (DIC). In an exemplary embodiment, the symmetrical anhydride is produced by reacting an Fmoc-protected amino acid with DIC. The amount of the various reactants in the reaction can and will vary. Typically, the amount of Fmoc-protected amino acid to carbodiimide will be a molar ratio ranging from about 1:1 to about 5:1. In one embodiment, the amount of Fmoc-protected amino acid to carbodiimide is a molar ratio of about 2:1. The symmetrical anhydride is reacted with the solid support I the presence of a nucleophilic catalyst. A non-limiting example of a nucleophilic catalyst suitable for reacting the symmetrical anhydride to the solid support includes 4-dimethylaminopyridine (DMAP). The molar ratio of the symmetrical anhydride to the solid support to the nucleophilic catalyst may range from about 10:1:0.1 to about 3:1:0.1. In one embodiment, the molar ratio of the symmetrical anhydride to the solid support to the nucleophilic catalyst may be about 5:1:0.1, In alternative embodiments, the first amino acid may be coupled to the solid support by first producing a halogen solid support. As depicted in FIG. 2 below, in this method, when $R^1$ is OH, a halogen solid support of Formula (Ib) is first produced. The halogen solid support is then reacted with an Fmoc-protected amino acid to produce a solid support comprising a compound of Formula (I), with an Fmoc-protected amino acid.

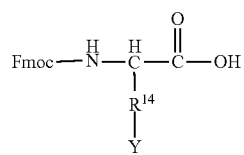

Incoming amino acid with Y side chain protecting group

Activation (DIEA)

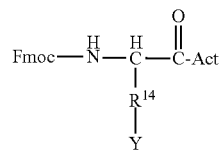

Coupling (Basic pH)

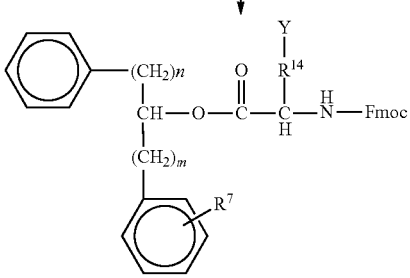

Solid support (1) with Fmoc-protected amino acid

FIG. 2

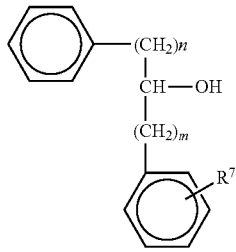

Solid support (I)

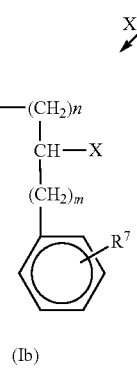

(Ib)

wherein:
$R^2$, $R^3$, $R^4$, $R^5$, $R^6$, $R^7$, m, and n are as described in section (I) for compounds having Formula (I), and X comprises a halogen.

The halogen solid support may be produced by contacting the solid support with X, which is a compound comprising a halogen. The choice of halogen can and will vary. In one embodiment, the halogen is selected from bromide and chloride. In an exemplary embodiment, the halogen is chloride. Non-limiting examples of compounds that comprise chloride may include acetyl chloride (i.e., $CH_3COCl$), thionyl chloride (i.e., $SOCl_2$), and phosphorous chloride (i.e., $PCl_3$). In a preferred alternative of the embodiment, the compound that comprises chloride is thionyl chloride. Generally speaking, the amount of solid support to the amount of thionyl chloride may be expressed as a weight ratio of from about 1:1 to about 1:10. In one exemplary embodiment, the amount of solid support to the amount of thionyl chloride is a molar ratio of about 1:3. The reaction is typically carried out in the presence of an organic solvent. For example, suitable solvents include, but are not limited to, alkane and substituted alkane solvents (including cycloalkanes), aromatic hydrocarbons, esters, ethers, ketones, combinations thereof, and the like. Specific organic solvents that may be employed, include, for example, acetonitrile, benzene, butyl acetate, t-butyl methylether, t-butyl methylketone, chlorobenzene, chloroform, chloromethane, cyclohexane, dichloromethane, dichloroethane, dichloroethene, diethyl ether, ethyl acetate, diethylene glycol, fluorobenzene, heptane, hexane, isobutylmethylketone, isopropyl acetate, methylethylketone, methyltetrahydrofuran, pentyl acetate, n propyl acetate, tetrahydrofuran, toluene, and combinations thereof. In an exemplary embodiment, the reaction is carried out in the presence of toluene.

The halogen solid support of Formula (Ib) is then coupled with an Fmoc-protected amino acid to produce a solid support comprising a compound of Formula (I), with an Fmoc-protected amino acid. The reaction is typically carried out in the presence of an organic solvent. For example, suitable solvents include, but are not limited to, alkane and substituted alkane solvents (including cycloalkanes), aromatic hydrocarbons, esters, ethers, ketones, combinations thereof, and the like. Specific organic solvents that may be employed, include, for example, acetonitrile, benzene, butyl acetate, t-butyl methylether, t-butyl methylketone, chlorobenzene, chloroform, chloromethane, cyclohexane, dichloromethane, dichloroethane, dichloroethene, diethyl ether, ethyl acetate, diethylene glycol, fluorobenzene, heptane, hexane, iso butylmethylketone, isopropyl acetate, methylethylketone, methyltetrahydrofuran, pentyl acetate, n propyl acetate, tetrahydrofuran, toluene, and combinations thereof. In an exemplary embodiment, the reaction is carried out in the presence of dichloromethane.

As depicted in the diagram above, for the coupling reaction the carboxyl group of the incoming amino acid is usually activated. Suitable activating compounds include carbodiimides, or those belonging to the aromatic oximes class or combinations thereof. In one embodiment, the carbodiimide is selected from dicyclohexylcarbodiimide (DCC), or diisopropylcarbodiimide (DIC). In another embodiment, the aromatic oxime is selected from 1-hydroxy-benzotriazole (HOBt), and 1-hydroxy-7-aza-benzotriazole (HOAt). In an exemplary embodiment, the activating compounds are DIG and HOBt. Other suitable activating compounds include HATU/HOAT, PyBOP/HOBT, or OPFP preactivated amino acids/HOBT. In an exemplary embodiment, the incoming amino acid is activated by contacting the amino acid with the DIEA activating compound. The amount of the various reactants in the coupling reaction can and will vary greatly.

After the solid support comprising Formula (I) has been loaded with the first amino acid, peptide elongation may be conducted with methods known in the art. In general, the method involves the use of the base labile Fmoc-amino protecting groups on the initial amino acid covalently coupled to the solid support and on each amino acid that is sequentially added to the growing peptide chain on the solid support. After each coupling step, the terminal Fmoc amino acid protecting group is then cleaved by base treatment to provide a free amine group ready for coupling the next amino acid in the next addition cycle. Acid-labile protecting groups generally protect the amino acid side chains. In this context, Fmoc chemistry is based on the orthogonal concept in the sense that the two protecting groups belong to independent classes (i.e., Fmoc is base labile and side chain protecting groups are acid labile) and can be removed by different mechanisms. The two groups may be removed, therefore, in any order in the presence of the other group.

Accordingly, with reference to FIG. 3, the synthesis of peptides by Fmoc-SPPS using the solid support of the invention involves the following general steps: (1) base deprotection of the solid support (1) with Fmoc-protected amino acid; (2) activation of an incoming amino acid such that its side chain is protected by an acid labile group; (3) coupling the amino acid to the growing polypeptide under basic pH; (4) repeating steps (1) to (3) until the desired polypeptide is synthesized; (5) Fmoc deprotection; (6) cleavage of the peptide from the support to yield the desired peptide acid.

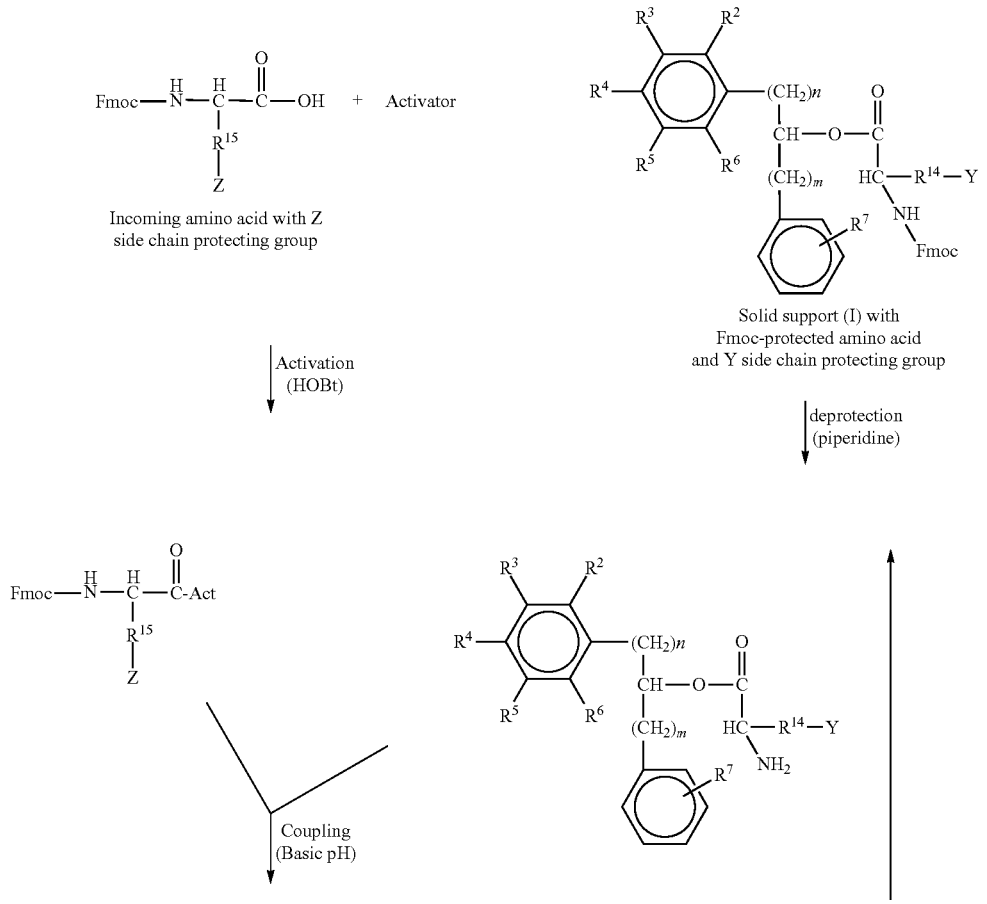

FIG. 3

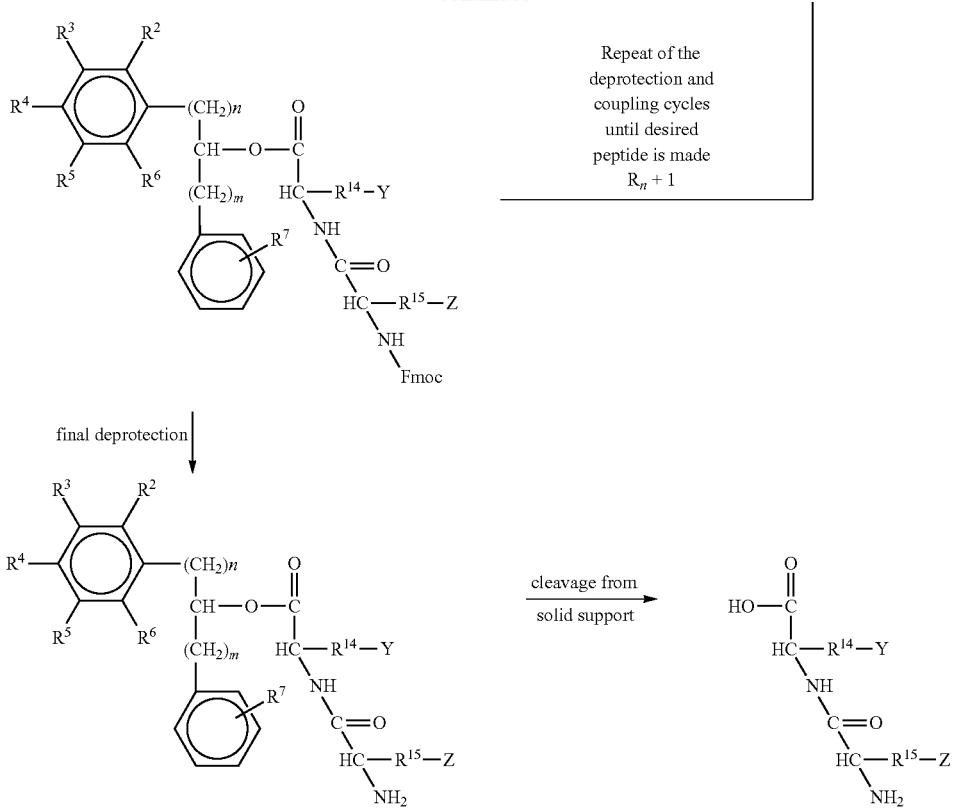

wherein:

$R^2$, $R^3$, $R^4$, $R^5$, $R^6$, $R^7$, m, and n are as described in section (I) for compounds having Formula (I).

Amine groups protected with Fmoc may be deprotected by treatment with an organic base. Suitable organic bases include piperidine, cyclohexylamine, 1,5-diazabicyclo[5,4,0]undec-5-ene, ethanolamine, pyrrolidine 1,8-diazabicyclo[5.4.0]undec-7-ene, diethylamine, morpholine, and mixtures thereof. In an exemplary embodiment, the base is piperidine. Typically, the amount of organic base used in Fmoc deprotection when the base is piperidine will range from about 5% to about 50% (v/v).

The Fmoc deprotection reaction is carried out in the presence of a solvent at approximately room temperature. Non-limiting examples of suitable solvents include anisole, dimethylformamide, dimethylsulfoxide, dimethyl acetamide, dichloromethane, N-methylpyrrolidinone, and mixtures thereof. A list of additional suitable solvents can be found in Tetrahedron Letters 39:8451-54 (1998), which is incorporated herein by reference in its entirety.

Each incoming amino acid that is added to the growing peptide chain is generally protected with an acid-labile side-chain protecting group. The acid-labile protecting groups used are typically based on butyl and trityl groups. For example, the group may be a tert-butyl moiety, such as, tert-butyl ethers for Ser, and Thr, tert-butyl esters for Asp, Glu, 2-Cl-trityl for Tyr, and Boc for Lys, His. Several suitable Fmoc-amino acids derivatives are commercially available.

As depicted in the diagram above, for the coupling reaction the carboxyl group of the incoming amino acid is usually activated. Suitable activating compounds include carbodiimides, or those belonging to the aromatic oximes class or combinations thereof. In one embodiment, the carbodiimide is selected from dicyclohexylcarbodiimide (DCC), or diisopropylcarbodiimide (DIC). In another embodiment, the aromatic oxime is selected from 1-hydroxy-benzotriazole (HOBt), and 1-hydroxy-7-aza-benzotriazole (HOAt). In an exemplary embodiment, the activating compounds are DIC and HOBt. Other suitable activating compounds include HATU/HOAT, PyBOP/HOBT, or OPFP preactivated amino acids/HOBT.

The amount of the various reactants in the coupling reaction can and will vary greatly. Typically the molar ratio of the solid support to the Fmoc-amino acid to the activating compound will range from about 1:1:1 to about 1:5:5. In one embodiment, the molar ratio of the solid support to the Fmoc-amino acid to the activating compound may be about 1:2:2.

The progress of amino acid couplings may be followed using a ninhydrin reaction, as described in the examples. The ninhydrin solution turns dark blue (positive result) in the presence of a free primary amine but is otherwise colorless (negative result).

Once the final amino acid has been added, the polypeptide may be cleaved from the solid support with a mild acid in the presence of appropriate scavengers to yield a peptide acid (or peptide amide as shown in FIG. 3). In general, the solid support will be treated with trifluoroacetic acid (TFA) in the presence of appropriate scavengers. The choice of scavengers is dependent on the amino acid sequence of the peptide. These scavengers include phenol, water, 1,2-ethanedithiol, and triisopropylsilane. In certain embodiments it may be desirable to release the peptide with all of the amino acids unprotected, with certain amino acids unprotected, with all amino acids protected, or to deprotect the amino acids while leaving the peptide covalently conjugated to the solid support. By varying the concentration of the mild acid, either a protected or unprotected peptide acid may be released from the solid support. The amount of TFA typically used for cleavage of the protected peptide from the solid support may range from about 1% to about 10% (v/v). More typically, the amount of TFA used for cleavage of the protected peptide from the solid support may range from about 5% to about 10% (v/v). The amount of TFA typically used for cleavage of the unprotected peptide from the solid support may be more than 10% (v/v).

The peptide is typically analyzed by chromatography, such as reverse phase HPLC or mass spectrometry after it is cleaved from the solid support. As will be appreciated by a skilled artisan the yield and purity can and will vary depending upon the peptide produced. The yield will generally range from about 40% to greater than about 90%. More typically, the yield will range from about 60% to greater than about 80%. The purity will generally range from about 65% to greater than about 99% as determined by HPLC.

While the solid support comprising Formula (I) may be utilized to produce a variety of peptides, it is particularly useful for the synthesis of peptide acids. In one alternative of this embodiment, the solid support may be used for synthesis of agonists or antagonists of guanylate cyclase type-c. A non-limiting example of an agonist or antagonist of guanylate cyclase type-c may include Linaclotide. In another alternative of this embodiment, the solid support may be used for synthesis of alpha-melanocyte stimulating hormone (α-MSH) or analogs thereof. Non-limiting examples of α-MSH analogs may include PT-141 (Bremelanotide), melanotan 1 and melanotan II. In yet another alternative of this embodiment, the solid support may be used for synthesis of brain natriuretic peptide (BNP), atrial natriuretic peptide (ANP), C-type natriuretic peptide (CTP), or analogs of BNP, ANP and CNP. A non-limiting example of an atrial natriueretic analog may include KT-220.

DEFINITIONS

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "base" is intended to mean an organic or inorganic substance with a pKa of greater than about 8.

"Boc" as used herein stands for tert-butyloxycarbonyl.
"DIC" as used herein stands for diisopropylcarbodiimide.
"DIEA" as used herein stands for diisopropylethylamine.
"DCM" as used herein stands for dichloromethane.
"DMF" as used herein stands for dimethylformamide.
"Fmoc" as used herein stands for 9-fluorenyl-methoxycarbonyl.

The term "halogen" as used herein alone or as part of another group refers to chlorine, bromine, fluorine, and iodine.

The term "hydrocarbyl" as used herein describes organic compounds or radicals consisting exclusively of the elements carbon and hydrogen. These moieties include alkyl, alkenyl, and alkynyl moieties. These moieties also include alkyl, alkenyl, and alkynyl moieties substituted with other aliphatic or cyclic hydrocarbon groups, such as alkaryl, alkenaryl and alkynaryl. Unless otherwise indicated, these moieties preferably comprise 1 to 20 carbon atoms.

"HOBT" as used herein stands for 1-hydroxybenzotriazole.
"NaBH$_4$" as used herein stands for sodium borohydride.
"NaOH" as used herein stands for sodium hydroxide.
"ON" as used herein stands for overnight.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom.

"TFA" as used herein stands for trifluoroacetic acid.

As various changes could be made in the above compounds, products and methods without departing from the scope of the invention, it is intended that all matter contained in the above description and in the examples given below, shall be interpreted as illustrative and not in a limiting sense.

EXAMPLES

The following examples detail the synthesis of the 2,4-dimethyl phenyl carbinal resin and the 2,4-dimethoxy phenyl carbinal resin and their use in peptide synthesis. Examples 1 and 2 describe the synthesis of the resins, Example 3 describes the formation of a resin chloride derivative of the resin and addition of a first amino acid, Example 4 details peptide synthesis methods and various resin derivatizations, and Examples 5 and 6 detail the synthesis of linaclotide and KT-220 peptides, respectively. The general synthesis scheme for the 2,4-dimethyl phenyl carbinal resin is shown below.

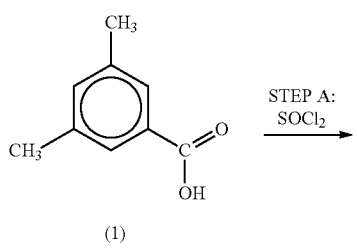

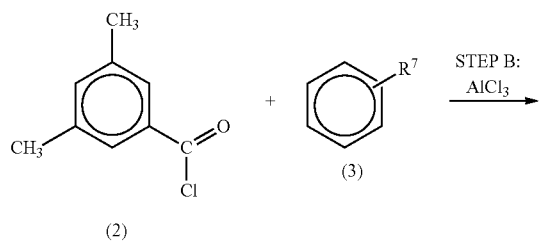

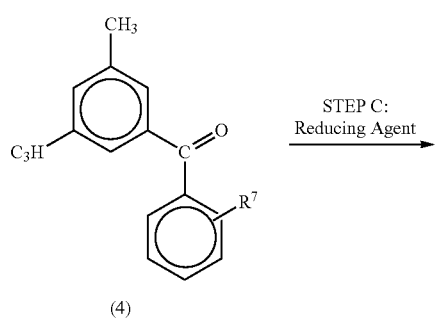

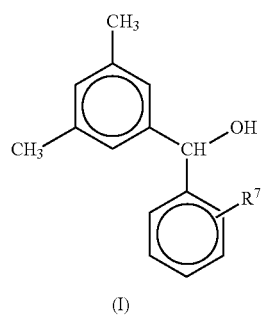

Example 1

Synthesis of 2,4-Dimethyl Phenyl Carbinal Resin

Step A—Synthesis of 2,4-dimethyl benzoyl chloride

The first step in the synthesis of the resin was to synthesize 2,4-dimethylbenzoyl chloride (compound 2 in the scheme) by reacting 2,4-dimethylbenzoic acid (DMBA) with a molar excess of thionyl chloride ($SOCl_2$) under N2. For this, 2,4-dimethylbenzoic acid was added with dichloromethane (DCM) solvent to a round bottom (RB) reactor with a nitrogen purge and cooled to 0° C. A 3-10 molar excess of thionyl chloride was then added dropwise under N2 while stirring and maintaining the temperature at ~0° C. Once all the thionyl chloride was added, the mixture was allowed to slowly return to room temperature while stirring. Stirring was continued for an additional 24 to 48 hours, until a clear homogeneous solution was obtained. The production of the product (compound 2) was monitored by IR and/or HPLC. The mixture was then evaporated to dryness under vacuum at low temperature to give a clear liquid oil. The resulting oil was co-evaporated three times with toluene by adding toluene and evaporating again under vacuum until a clear liquid/oil was produced.

A number of preparations were prepared in which the molar ratio of DMBA to $SOCl_2$ and reaction times were varied. Table 1 presents the reaction conditions, as well as the amount and purity of the product.

TABLE 1

| | Synthesis of Compound 2 | | | | | |
|---|---|---|---|---|---|---|
| | Amount of compound 1 | Amount of thionyl chloride | Molar ratio | Time in reactor | Amount of compound 2 | Purity of compound 2 |
| Prep 1 | 22.53 g (0.15 mole) | 1.25 mole | 8.3 | O/N | 22.75 g (0.135 moles) | 77.53% |
| Prep 2 | 22.53 g (0.15 mole) | 1.25 mole | 8.3 | O/N (24 hrs) | 23.92 g (0.142 mole) | 94.54% |
| Prep 3 | 22.4 g (0.15 mole) | 0.6 mole | 4 | O/N (~22 hrs) | 23 g (0.141 mole) | 94.32% |
| Prep 4 | 120.14 g (0.8 mole) | 3.2 moles) | 4 | O/N | 131.65 g (0.78 mole) | 78.6% |
| Prep 5 | 120.14 g (0.8 mole) | 3.2 moles | 4 | O/N (48 hrs) | 167.6 g (0.99 mole) | 81.9% |

Step B—Synthesis of 2,4-dimethyl phenyl ketone resin

The second step in the synthesis of the resin was to synthesize the 2,4-dimethylphenyl ketone resin (compound 4) by reacting the 2,4-dimethylbenzoyl chloride (compound 2) with 1% divynilbenzene cross linked polystyrene resin (200-400 mesh) (compound 3). The polystyrene resin was added with dichloromethane (DCM) or dichloroethene (DCE) solvent to a round bottom (RB) reactor and cooled to 0° C. with a nitrogen purge. The product from step A (i.e., 2,4-dimethylbenzoyl chloride in solvent) was then added to the reactor at a ratio of 8 mmole of 2,4-dimethylbenzoyl chloride per gram of resin, and the mixture cooled again to ~0° C. under nitrogen purge with continuous stirring. $AlCl_3$ catalyst was slurried in DCM or DCE and added in portions over a 10-20 minute time period to the reaction mixture while keeping the mixture at ~0° C. The mixture was stirred O/N (20 to 48 hours) and the temperature of the mixture was allowed to come to room temperature. The next day, methanol that was cooled to 0° C. was added to the reaction mixture; the volume of methanol was no more than 50% of the solvent volume. The resin was then filtered, and washed three times each with cold methanol, methanol+solvent (2:1), solvent, then methanol again, and then dried to yield the ketone resin. The production of the ketone resin was monitored by IR.

Table 2 presents the different reaction conditions tested and the amount of resin produced under the different conditions. For example, Preps 3 and 4 were identical except that synthesis was performed in the presence of either DCE or DCM. There was no difference in yield of the product with the two different solvents.

TABLE 2

Synthesis of Compound 4

| | Amount of compound 2 | Amount of compound 3 | Amount of catalyst | Weight ratio of 2:3:$AlCl_3$ | Solvent | Time in reactor | Wt of compound 4 |
|---|---|---|---|---|---|---|---|
| Prep 1 | 22.7 g (0.150 mole) | 18.75 g (8 mmole acid/g resin) | 16 g (6.4 mmole $AlCl_3$/g resin) | 1:0.8:0.7 | DCE 187 ml | ~48 hrs | 26.87 g |
| Prep 2 | 23.92 g (~0.15 mole) | 18.75 g (8 mmole acid/g resin) | 16 g (6.4 mmole $AlCl_3$/g resin) | 1:0.8:0.7 | DCE 200 ml | ~48 hrs | 28.95 g |
| Prep 3 | 11.5 g (0.075 mole) | 9.4 g (8 mmole acid/g resin) | 8.02 g (6.4 mmole $AlCl_3$/g resin) | 1:0.8:0.7 | DCE 170 ml | ~24 hrs | 12.81 g |
| Prep 4 | 11.5 g (0.075 mole) | 9.4 g (8 mmole acid/g resin) | 8.02 g (6.4 mmole $AlCl_3$/g resin) | 1:0.8:0.7 | DCM 170 ml | ~24 hrs | 13.08 g |
| Prep 5 | 167.57 g (~0.8 mole) | 100 g (~8 mmole acid/g resin) | 85.32 g (6.4 mmole $AlCl_3$/g resin) | 1:0.6:0.5 | DCM 1300 ml | ~20 hrs | 148.82 g |

Step C—Reduction of the 2,4-dimethyl phenyl ketone resin

The third step in the synthesis of the resin was to reduce the ketone resin to an alcohol resin to produce compound (I) in the scheme. A number of synthesis methods were tested in which the reducing agent, the solvent, time of the reaction and washing conditions were varied. The various methods are presented below.

Method A.

2,4-dimethyl phenyl ketone resin (2 g) from step B in 30 ml tetrahydrofuran (THF) solvent was heated to 65° C. in a 3-necked RB-flask with mechanical stirring and N2 condenser. $LiBH_4$ reducing agent (0.5 g; 25% by weight of resin) was added. Samples were taken approximately every hour for about six hours for IR monitoring of the reaction. Because the reaction was not completed after by six hours, an additional 0.5 g of $LiBH_4$ was added, the heat was shut off, and the reaction allowed to proceed overnight. The next day, the reaction was still not completed, and another 0.5 g of $NaBH_4$ was added after returning the reaction to 65° C. IR analysis revealed that the ketone was not reduced, and the reaction was stopped.

Method B.

2,4-dimethyl phenyl ketone resin (2 g) from step B in 30 ml anhydrous ethanol (EtOH) solvent was heated to 65° C. in a 3 necked RB-flask with mechanical stirring and $N_2$ condenser. $NaBH_4$ reducing agent (0.5 g; 25% by weight of resin) was added. The reaction was heated for three hours then allowed to return to room temperature overnight. IR analysis revealed that the reaction did not proceed, so the mixture was heated again to 65° C. and allowed to continued for another 4 hours. Then 0.25 g of $NaBH_4$ was added, the heat was turned off, and the reaction was allowed to continue over the weekend (~60 hours). The resin was filtered, washed with $H_2O$ twice, with MeOH twice, with DCM twice, and then dried. IR analysis revealed that the ketone was not reduced.

Method C.

2,4-dimethyl phenyl ketone resin (2 g) from step B in a 4:1 mixture of DMF/EtOH (32 ml DMF and 8 ml EtOH) solvent was heated to 65° C. in a 3 necked RB-flask with mechanical stirring and $N_2$ condenser. $NaBH_4$ reducing agent (0.6 g; 30% by weight of resin) was added in DMF/EtOH. The reaction was heated for seven hours then allowed to return to room temperature overnight (~20 hrs). IR readings showed that the reaction did not progress, so the mixture was heated again to 65° C., 0.3 g $NaBH_4$ was added, and the reaction allowed to progress for another 45 hours. The resin was filtered, washed with DMF twice, $H_2O$ twice, MeOH twice, DCM twice and then dried. IR analysis showed that the resin was reduced.

Method D.

2,4-dimethyl phenyl ketone resin (16 g) from step B in a 4:1 mixture of DMF/EtOH (96 ml DMF and 24 ml EtOH) solvent was heated to 65° C. in a 3 necked RB-flask with mechanical stirring and N2 condenser. $NaBH_4$ reducing agent (4.8 g; 30% by weight of resin) was added in 20 ml 50% EtOH/MeOH. The reaction was heated for ~24 hours. The reaction was then stopped by adding acetone and stirring at RT for 20-30 min. The resin was filtered and washed with DMF (2×), $H_2O$ (2×), 50% DMF/$H_2O$ (2×), MeOH (2×), DCM (2×), and dried. IR readings showed that ketone peak was still present, so the resin (16 g) was returned to the reactor with 120 ml 4:1 DMF/EtOH and 4.8 g $NaBH_4$ dry powder. Reaction was complete after one hour at 65° C. in the reactor.

Method E.

2,4-dimethyl phenyl ketone resin (7 g) from step B in 70-75 ml DMF solvent was heated to 75 C.° in a 3 necked RB-flask with mechanical stirring and N2 condenser. $NaBH_4$ reducing agent (2.8 g; 40% by weight of resin) was added. After 4 hrs, IR results showed that reaction did not occur. $NaBH_4$ reducing agent (2.8 g; 40% by weight of resin) was added again, and the reaction allowed to continue O/N. However, the reaction did not occur again. A 3:1 mixture of DMF/EtOH (70-75 ml DMF and 25 ml EtOH) solvent was added and the mixture was heated to 75° C. for another 4 hours, at which time IR analysis showed that the reaction was almost complete. These results show that EtOH was required for the reaction to occur. The reaction was then stopped by adding acetone and stirring at RT for 20-30 min. The resin was filtered and washed with DMF (2×), $H_2O$ (2×), 50% $DMF/H_2O$ (2×), MeOH (2×), DCM (2×), and dried. The washes were made with large volumes and were performed for long times.

As a result of these experiments, the following procedure was selected for reducing the ketone resin to the alcohol form: The ketone resin was stirred with DMF+MeOH (3:1 to 4:1) at 70-75° C. and treated with $NaBH_4$ (30% by weight excess of resin) by heating at 70-75° C. for 4-6 hours. The reaction was monitored by IR method. After completion of the reaction at 70-75° C., the mixture was allowed to cool to room temperature. It was then quenched with acetone (80-100 ml) and after stirring for approximately one hour, it was filtered, washed with DMF (2×), $H_2O$ (3×), 50% DMF+$H_2O$ (3×), DMF (2×), MeOH (2×), DCM (2×), and dried to yield the 2,4-dimethyl phenyl carbinal (DMPC) resin. The substitution of the alcohol group was determined by elemental analysis.

Example 2

Synthesis of 2,4-dimethoxy phenyl carbinal resin

Synthesis of this resin was essentially as described for synthesis of 2,4-dimethyl phenyl carbinal resin described in steps A and B of Example 1 above with the obvious difference that 2,4-dimethoxybenzoic acid instead of the dimethylbenzoic acid was used as a starting point. The dimethoxy phenyl ketone resin was reduced (step C) using different methods as described below.

Method A.

2,4-dimethoxy phenyl ketone resin (10 g) from step B in a 3:1 mixture of DMF/EtOH (75 ml DMF and 25 ml EtOH) solvent was heated to 70° C. in a 3 necked RB-flask with mechanical stirring and $N_2$ condenser, 3 g of $NaBH_4$ (30% by weight of resin) were added in powder form and the flask rinsed with MeOH. The reaction was heated for another 4 hours, at which time IR analysis showed that the reaction was not complete, with a ketone peak still there. The reaction was allowed to continue for an additional 21 hours at room temperature, but the results were the same.

Method B.

2,4-dimethoxy phenyl ketone resin (8.86 g) from step B in a 3:1 mixture of DMF/EtOH (60 ml DMF and 20 ml EtOH) solvent was heated to 70° C. in a 3 necked RS-flask with mechanical stirring and N2 condenser. 2.66 g of $NaBH_4$ (30% by weight of resin) were added in powder form and the flask rinsed with MeOH. The reaction was heated for ~23 hours, at which time IR analysis showed that the reaction was complete. The reaction was then quenched with 20 ml of acetone and after stirring for 30 min, it was filtered through a 40-60 micron filter, washed with DMF (3×), $H_2O$ (3×), 50% DMF+$H_2O$ (3×), DMF (2×), MeOH (3×), DCM (3×), MeOH (3×), DCM (3×), and dried.

Example 3

Production of Resin Chloride and Coupling with the First Amino Acid 2,4-dimethyl phenyl carbinal resin (4 g) from Example 1 was added to an RB-reactor set up with mechanical stirring. 40 ml of Toluene was added, followed by 0.873 moles $SOCl_2$. The reaction mixture was heated to 70° C. for about 12 hours, and then cooled to room temperature. The resulting resin was washed once with toluene, three times with DMF, three times with IPA, three times with DOM, then twice with IPA again, then filtered and dried under vacuum before IR analysis.

200 mg of the resin chloride was mixed with 200 mg Fmoc-Tyr (OtBu) in 3.5 ml DCM. 3 drops of DIEA were then added and the reaction mixture stirred at room temperature. The resin was then filtered and washed twice with DMF, twice with IPA, and twice with DCM. Resin substitution was measured at 0.144 mm/g.

Example 4

Peptide Synthesis Methods and Various Derivations of the DMPC Resin

Peptide synthesis procedures followed standard procedure described in the art, and were as follows. The first Fmoc-protected amino acid was loaded on the resin using either the Symmetrical anhydride method, or the DCB method as described in Table 3 below. Resin substitution was then assayed using the diaza(1,3)bicyclo[5.4.0]undecane (DBU) base method. This method comprises uncoupling Fmoc from the resin with DBU, and measuring the UV absorbance of the fulvene derivative of Fmoc.

TABLE 3

| Methods for coupling the first amino acid | |
|---|---|
| Symmetrical anhydride method | DCB method |
| 1. Prepare amino acid symmetrical anhydride using DIC in DCM | 1. Resin is swelled in DMF. |
| 2. Swell resin in DMF | 2. Fmoc-amino acid is added to the resin in DMF, followed by pyridine |
| 3. Add Fmoc-AA anhydride from step 1 to resin in DMF | 3. Add 2,6-dichlorobenzoyl chloride (DCB) |
| 4. Add 2,4-dimethylamino pyridine (DMAP) and stir | 4. Wash and shrink down resin |
| 5. Wash resin with DMF | |
| 6. Determine extent of loading | |
| 7. Add benzoic anhydride in DMF and agitate | |
| 8. Wash and shrink down resin | |
| 9. Unreacted resin hydroxyl groups are capped | |

A number of derivations were performed with various amino acids and methods of loading. Table 4 presents the protected amino acids, the method of coupling, and the substitution rate for each derivation.

TABLE 4

Derivations

| Prep # | Amino acid | Coupling method | Substitution mmole/g |
|---|---|---|---|
| 1 | Fmoc-Gly | DCB | 1.135 mmole/g |
| 2 | Fmoc-Gly | DCB | 0.83 mmole/g |
| 3 | Fmoc-Lys (Mtt) | DCB | 0.614 mmole/g |
| 4 | Fmoc-Tyr (OtBu) | DCB | 1.06 mmole/g |
| 5 | Fmoc-Tyr (OtBu) | DCB | 1.01 mmole/g |
| 6 | Fmoc-Tyr (OtBu) | Symmetrical anhydride (SA) | 1.08 mmole/g |
| 7 | Fmoc-Tyr (OtBu) | Symmetrical anhydride (SA) | 0.93 mmole/g |
| 8 | Fmoc-Arg (Pbf) | Symmetrical anhydride (SA) | 0.5467 mmole/g |

All the additional amino acids in the peptide sequences (presented in Examples 4 and 5) were coupled following the synthesis protocol presented in Table 5 using the DIC/HOBt coupling method. The progress of the coupling reaction was monitored using a ninhydrin test (see Table 6), which detects free amines. When the reaction was complete, the resin was filtered and washed with DMF (2 times), isopropanol (IPA; 2 times), DMF (2 times) and DCM (2 times) according to the synthesis protocol (see Table 5). After coupling, the N-α-Fmoc group was removed with 20% piperidine in DMF, and the assembled peptide was cleaved from the resin with TFA scavenger.

TABLE 5

Peptide Synthesis Protocol.

| Step No. | Reagents/Solvents* | Times × Minutes |
|---|---|---|
| 1 | DMF Wash | 1 × 3 minutes |
| 2 | 20% Piperidine in DMF | 2 × 10-20 minutes |
| 3 | DMF Wash | 2 × 3 minutes |
| 4 | IPA wash | 2 × 3 minutes |
| 5 | DMF Wash | 2 × 3 minutes |
| 6 | DCM Wash | 2 × 3 minutes |
| 7 | Coupling in DMF + DCM (3:1 to 5:1) | 4 hours to overnight |
| 8 | DMF wash | 2 × 3 minutes |
| 9 | IPA wash | 2 × 3 minutes |
| 10 | DMF wash | 2 × 3 minutes |
| 11 | DCM Wash | 2 × 3 minutes |

*6-8 ml/g of resin.

TABLE 6

Ninhydrin Test.*

Reagents needed:

0.5 g ninhydrin in 10 ml ethanol
40.0 g phenol in 10 ml ethanol
2 ml 0.001M KCN in 10 ml pyridine
Method:

1. Place a 3-5 mg sample of the resin in a culture tube and add 3 drops of each reagent (ninhydrin reagent, phenol reagent, KCN reagent).
2. Place culture tube (with resin and reagents) in a heat source (100-110° C.) for 2-5 minutes and observe the color.
Result:

A positive test for amino acids (free amine group) is indicated by a blue-green to blue color. A negative test for free amino group is indicated by an amber color.

*E. Kaiser, Analytical Biochemistry, 34, 595-598, 1970,

Example 5

Comparing Synthesis of Various Peptides on Wang and DMPC (or DMBH) Resins

Various peptides were synthesized as described above using the commercially available Wang resin, and the DMPC resin of the invention. Table 7 presents the length of the peptides synthesized, and the yield and purity of the peptides synthesized when using the Wang resin versus the DMPC resin of the invention. Table 8 presents a summary of cleavage data for peptide 1 at various concentrations of TFA.

TABLE 7

Synthesis of peptides using two solid supports

| Peptide | Sequence length | Synthesis scale | DMPC resin % yield | Purity | Wang resin % yield | Purity |
|---|---|---|---|---|---|---|
| Peptide-1 | 8 | 2.8 mm | 100% | 72.24% | — | — |
| Peptide-2 | 7 | 3.3 mm | 100% | 67.06% | 98.16% | 52.95% |
| Peptide-3 | 24 | 5.5 mm | 44% | 47.47% | 64.86% | 17.29% |
| Peptide-4 | 32 | 2.12 mm | 91% | 12.00% | 69.80% | 16.80% |
| Peptide-5 | 14 | 2.75 mm | 98% | 76.00% | 94.60% | 13.77% |
| Peptide-6 | 37 | 3.0 mm | 100% | 58.81% | 86.80% | 32.30% |
| Peptide-7 | 17 | 6.5 mm | 88% | 91.42% | — | — |

TABLE 8

Peptide-1 resin cleavage data

| Peptide Resin Sample | % TFA | # of major peaks after cleavage | RRT (min) of peaks, (% Purity) | Amount of crude peptide, mg |
|---|---|---|---|---|
| 200 mg | 25 | 3 | 9.895 (75.637), 14.432 (13.472), 16.305 (4.440) | 50 |
| 200 mg | 50 | 3 | 9.999 (55.515), 16.537 (12.257), 18.272 (20.420) | 50 |
| 200 mg | 75 | 3 | 9.930 (74.011), 15.351 (15.395), 16.571 (3.288) | 30 |
| 200 mg | 5 | 2 | 18.777 (75.347), 19.057 (22.119) | 80 |
| 200 mg | 10 | 2 | 18.827 (74.460), 19.098 (22.594) | 70 |
| 200 mg | 15 | 5 | 10.152 (1.665), 18.208 (42.081), 18.431 (10.842), 18.803 (32.195), 19.074 (7.255) | 70 |
| 200 mg | 20 | 4 | 18.275 (11.255), 18.497 (3.473), 18.842 (65.660), 19.110 (17.691) | 60 |

What is claimed is:

1. A compound of Formula (I):

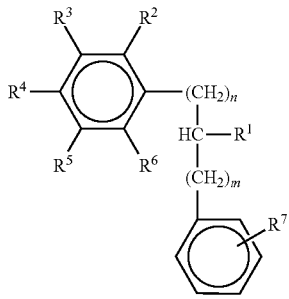
(I)

wherein:
  $R^1$ is $OR^8$;
  $R^3$, $R^5$, and $R^6$ are independently selected from the group consisting of hydrogen, hydrocarbyl, and substituted hydrocarbyl;
  $R^2$ and $R^4$ are each $\{-\}(CH_2)_sCH_3$, wherein s is an integer from 0 to 5;
  $R^7$ and the phenyl ring to which it is attached together comprise a solid support comprising at least one polymer;
  $R^8$ is selected from the group consisting of hydrogen, a protecting group, an amino acid residue, a hydrocarbyl, a substituted hydrocarbyl, and a peptide; and
  n and m are independently integers from 0 to 5.

2. The compound of claim 1, wherein $R^3$, $R^5$, and $R^6$ are each hydrogen.

3. A compound of Formula (I):

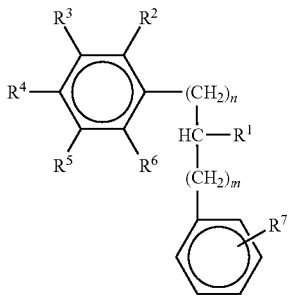
(I)

wherein:
  $R^1$ is $OR^8$;
  $R^2$, $R^3$, and $R^5$ are independently selected from the group consisting of hydrogen, hydrocarbyl, and substituted hydrocarbyl;
  $R^4$ and $R^6$ are each $\{-\}(CH_2)_sCH_3$, wherein s is an integer from 0 to 5;
  $R^7$ and the phenyl ring to which it is attached together comprise a solid support comprising at least one polymer;
  $R^8$ is selected from the group consisting of hydrogen, a protecting group, an amino acid residue, a hydrocarbyl, a substituted hydrocarbyl, and a peptide; and
  n and m are independently integers from 0 to 5.

4. The compound of claim 3, wherein $R^2$, $R^3$, and $R^6$ are each hydrogen.

5. A compound comprising Formula (I):

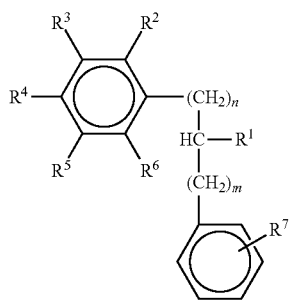
(I)

wherein:
  $R^1$ is $OR^8$;
  $R^2$, $R^3$, $R^4$, $R^5$, and $R^6$ are independently selected from the group consisting of hydrogen and hydrocarbyl, provided, however, that at least two of $R^2$, $R^3$, $R^4$, $R^5$, and $R^6$ are other than hydrogen;
  $R^7$ and the phenyl ring to which it is attached together comprise a solid support comprising at least one polymer;
  $R^8$ is selected from the group consisting of hydrogen, a protecting group, an amino acid residue, a hydrocarbyl, a substituted hydrocarbyl, and a peptide; and
  n and m are independently integers from 0 to 5.

6. The compound of claim 5 comprising the following structure:

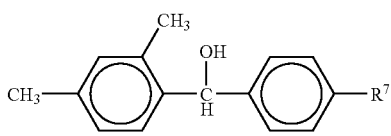

wherein $R^7$ is as defined in claim 5.

* * * * *